United States Patent
Jones et al.

[11] Patent Number: 5,892,141
[45] Date of Patent: Apr. 6, 1999

[54] METHOD AND APPARATUS FOR ANALYSIS OF PARTICULATE CONTENT OF GASES

[75] Inventors: Barbara L. Jones, King's Lynn; Kenneth W. Peter, Cambs, both of United Kingdom

[73] Assignee: Sun Electric U.K. Limited, King's Lynn, United Kingdom

[21] Appl. No.: 753,105

[22] Filed: Nov. 20, 1996

[30] Foreign Application Priority Data

Nov. 21, 1995 [GB] United Kingdom ............. 9523812

[51] Int. Cl.$^6$ ................................. G01N 29/02
[52] U.S. Cl. ........................... 73/24.03; 73/28.04
[58] Field of Search ................. 73/24.03, 28.04, 73/28.01

[56] References Cited

U.S. PATENT DOCUMENTS

| | | | |
|---|---|---|---|
| 3,473,118 | 10/1969 | Tassicker et al. ............ | 73/28.01 X |
| 3,478,573 | 11/1969 | King, Jr. . | |
| 3,561,253 | 2/1971 | Dorman . | |
| 3,715,911 | 2/1973 | Chuan . | |
| 4,041,768 | 8/1977 | Gibert et al. . | |
| 4,154,088 | 5/1979 | Werner . | |
| 4,166,379 | 9/1979 | Bradshaw . | |
| 4,248,386 | 2/1981 | Morle ............................ | 239/707 |
| 4,294,105 | 10/1981 | Kelly ............................ | 73/28.01 |
| 4,309,199 | 1/1982 | Suzuki . | |
| 4,446,720 | 5/1984 | Sinclair . | |
| 4,561,286 | 12/1985 | Sekler et al. . | |
| 4,656,832 | 4/1987 | Yukihisa et al. ............... | 60/303 |
| 4,764,186 | 8/1988 | Langer . | |
| 4,827,760 | 5/1989 | Saito ........................ | 73/864.71 X |
| 4,917,499 | 4/1990 | Champetier et al. ............ | 374/14 |
| 5,042,288 | 8/1991 | Vig ............................ | 73/24.03 X |
| 5,056,355 | 10/1991 | Hepher et al. ................ | 73/24.03 |
| 5,110,747 | 5/1992 | Pataschnick et al. .......... | 436/133 |
| 5,279,970 | 1/1994 | Potashnick et al. ........... | 73/28.04 X |
| 5,349,844 | 9/1994 | Lilienfeld .................... | 73/24.03 X |
| 5,476,002 | 12/1995 | Bowers et al. ................ | 73/24.01 |
| 5,511,409 | 4/1996 | Knaebel ....................... | 73/28.04 |
| 5,571,946 | 11/1996 | Kushi et al. .................. | 73/28.04 X |
| 5,604,335 | 2/1997 | Ishaya ........................ | 73/24.03 X |

FOREIGN PATENT DOCUMENTS

| | | | |
|---|---|---|---|
| 191639 | 7/1992 | Japan ............................ | 73/24.03 |
| 1564520 | 5/1990 | U.S.S.R. ........................ | 73/24.03 |

OTHER PUBLICATIONS

*Patent Abstracts of Europe* GB 02270564A Mar. 16 1994 "Analyte Identification Using Oscillating Sensors".

*Primary Examiner*—Thomas P. Noland
*Attorney, Agent, or Firm*—Emrich & Dithmar

[57] ABSTRACT

A method and apparatus for analysis of particulate content of gases, applicable to the quantitative and qualitative analysis of vehicle engine emissions, includes sampling, removing particles and analysis of the removed particles. Sampling is effected by electrostatic precipitation using a catalyst-coated piezoelectric crystal. The analysis of the removed particles is effected by heating the crystal in an oxidizing atmosphere to oxidize the deposited particles. Connection of the crystal to an oscillation circuit enables the frequency of oscillation of the crystal to be monitored. Changes in the frequency of oscillation are interpreted to provide quantitative and qualitative analysis of particles deposited and subsequently oxidized.

16 Claims, 3 Drawing Sheets

METHOD AND APPARATUS FOR ANALYSIS OF PARTICULATE CONTENT OF GASES

DESCRIPTION OF THE PRIOR ART

1. Field of the Invention

This invention relates to a method and apparatus for analysis of particulate content of gases. An example of the application of the invention is to the qualitative and quantitative analysis of emissions from internal combustion engines, particularly vehicle engines, but the invention is applicable also more widely than in the automotive field.

2. Background of the Invention

The analysis of particulate matter in air and other gases is performed in a wide variety of industries and applications. In the automotive sector, exhaust emissions from automobiles and cars and trucks and lorries are measured during and post manufacture and in the aftermarket to ensure compliance with increasingly restrictive official regulations. The particulate matter (soot) generated by diesel engines is a focus for legislative control and is at present the subject of studies into its effects on public health. It is likely that supplementary regulations relating to the particulate content in vehicle emissions will compel automotive and other manufacturers to investigate the means to reduce such levels in original equipment. Likewise, ensuring compliance of engines in use in the aftermarket may entail a modification to the tests carried out on a compulsory basis in many countries to determine compliance with official requirements.

Currently available equipment for determination of particulate content of engine emissions, as used in Europe in the aftermarket, is based upon the measurement of opacity using a comparatively simple and inexpensive instrument. Another technique uses a volumetrically-controlled sample of engine emission gas which is drawn through a filter element and the degree of discoloration of the filter element is used as an index for the amount of soot emitted. Both these techniques are unsuitable for the quantitative analysis of sub-micron particles and provide no qualitative information, as such, at all.

As regards engine emission tests carried out during and after engine manufacture, these are more complex. Exhaust emissions are tested on a chassis dynamometer or engine test stand using the CVS (controlled volume sampling) method. In this method, the exhaust gases are diluted with filtered ambient air and extracted with a blower and applied to a standardized test procedure. The dilution inhibits condensation and agglomeration effects during sample collection. Dilution also holds the sample temperature at the level required for particulate measurement. Several techniques are available for particulate measurement, including gravimetric measurement, differential mobility analysis and condensation core counting. At present, the gravimetric technique is the most widely used means of assessment, but it lacks sensitivity at low particulate levels and measurement time is lengthy. All these available techniques involve relatively large and expensive equipment, which arises particularly as a result of the use of the dilution system, which simulates the physical and chemical processes which the particulate emissions undergo in the atmosphere.

As to laboratory techniques for particulate measurement, many methods have been developed including the use of the quartz crystal microbalance and the electrostatic precipitator. To the best of the Applicant's knowledge these techniques have not been applied to the qualitative and/or quantitative analysis of automotive emissions and the like.

There is disclosed in U.S. Pat. No. 3,478,573 (King) a piezoelectric crystal having an integral heater and suitable for use in measuring devices, such as gas analyzers. An electronic oscillator is controlled by the piezoelectric material. A coating on the piezoelectric material is adapted to interact with at least one component of a fluid to be analyzed and the resulting changes in the frequency of the piezoelectric material as it interacts with the fluid are monitored for analytical purposes. The process is subject to the limitations evident from the development of the present invention, including inferior sensitivity and less clear-cut simplicity of construction as compared with the analytical desorbtion process of the embodiments of the present invention.

There is disclosed in U.S. Pat. No. 5,056,355 (Hepher) a device for monitoring dust or other particulate material in gas and comprising the use of a piezoelectric sensor and the step of monitoring variations in the resonant frequency of the sensor as induced by the aggregation of dust on the sensor. The system of this prior proposal is likewise subject to the limitation highlighted by the embodiments of the present invention and arising from the use of a technique in which the frequency monitoring step is applied to the process of particulate aggregation or addition to the sensor, as opposed to the converse system employed in the embodiments of the invention.

GB-A-2 270 564 (GEC Marconi) discloses a method of identifying fluid materials or analytes using a piezoelectric crystal oscillator. The system operates on the basis of monitoring a step change in the concentration of the analyte, leading to a characteristic frequency change enabling identification of the analyte. The method includes an embodiment using a reverse step in concentration change. However, this disclosure, in common with the other prior proposals known to the applicants, lacks any suggestion of the technical merit of monitoring the frequency change resulting from the inverse step of particulate desorbtion or removal from the piezoelectric substrate, with its attendant advantages as disclosed herein.

U.S. Pat. Nos. 3,561,253, 4,561,286, 4,041,768, and 4,446,720 all disclose particulate mass measurement systems which monitor frequency changes in oscillating piezoelectric devices on which particulate matter is deposited, such as by electrostatic deposition. However, none of these patents discloses or suggests a system in which the technical benefits of applying the analytical step to a process for the removal, partial or complete, of the particulate matter from the piezoelectric substrate are realized, nor indeed a process by which such an inverse step could be accomplished in a piezoelectric device while monitoring frequency changes.

SUMMARY OF THE INVENTION

An object of the present invention is to provide a method and apparatus, particularly but not exclusively applicable to the qualitative and/or quantitative analysis of automotive emissions, providing improvements in relation to currently available equipment, notably in relation to compactness of the apparatus and/or simplicity or speed of the method and/or cost of the apparatus and/or the method, or other improvements disclosed herein or generally.

According to the invention a method and apparatus for the analysis of particulate content of gases comprises the steps of sampling the gas, removing particles from the gas sample, and subjecting the removed particles to analysis.

In accordance with the invention, the step of removal of the particles from the gas sample comprises causing the particles to be deposited on a substrate. Further in accordance with the invention, the step of analysis comprises causing at least some of the deposited particles to be removed from the substrate and the application of a measurement technique to this step of removal in order to determine qualitative or quantitative information concerning the particulate content of the gas to be analyzed.

The steps of sampling and removal and analysis correspond to steps of analysis known from the use of an electrostatic precipitator. The additional steps of causing the particles to be deposited on a substrate and some at least of these to be subsequently removed while analysis takes place, in accordance with the invention, enable a simple and rapid determination of information concerning the qualitative and/or quantitative content of the gas to be analyzed, thereby reducing the need for subsequent flushing or cleaning before repeat use.

Thus, in one embodiment, the step of removal of the particles is carried out by means of an electrostatic precipitation technique employing a metal-coated piezoelectric crystal forming an anode in the precipitation step. Then, some at least of the particles deposited on the electrode are removed in an oxidizing step merely by application of heat and an oxidizing atmosphere to the piezoelectric crystal, so that qualitative and quantitative information can be obtained concerning the particles deposited.

This is achieved by connecting the electrode to an oscillator circuit and monitoring the changes in the frequency of oscillation as the particles are initially deposited and subsequently removed. Interpretation of the profile of the graph of rate of change of mass of the electrode provides a basis for determining the identity and/or quantitative presence of materials deposited and removed from the electrode.

Accordingly, the embodiments of the invention provide a method and apparatus whereby a relatively simple item of electrical equipment can obtain both qualitative and quantitative data relating to particulate content of gases on a relatively rapid basis.

It is believed to be novel to utilize a piezoelectric crystal device as a basis for performing (on a frequency basis) a process of thermo-gravimetric analysis of the particulate content of a gas sample. The piezoelectric crystal permits gravimetric monitoring of the process of thermal (oxidative, or otherwise chemically) removal of particulate material deposited thereon. The use of this removal or desorbtion step as the basis for analysis means that a thermo-gravimetric basis for analysis (which is novel in relation to piezoelectric devices) can be utilized, which enables frequency profile analysis to be performed, both in relation to particulate size and particulate identity.

While the principal applications of the invention are expected to be in the testing of automobile exhaust emissions, both at the time of manufacture and in the automotive aftermarket, it is expected that a variant of the embodiments could be developed for environmental or industrial pollution monitoring.

BRIEF DESCRIPTION OF THE DRAWINGS

Embodiments of the invention will now be described of example with reference to the accompanying drawings in which.

DESCRIPTION OF THE PREFERRED EMBODIMENT

Figure 1:
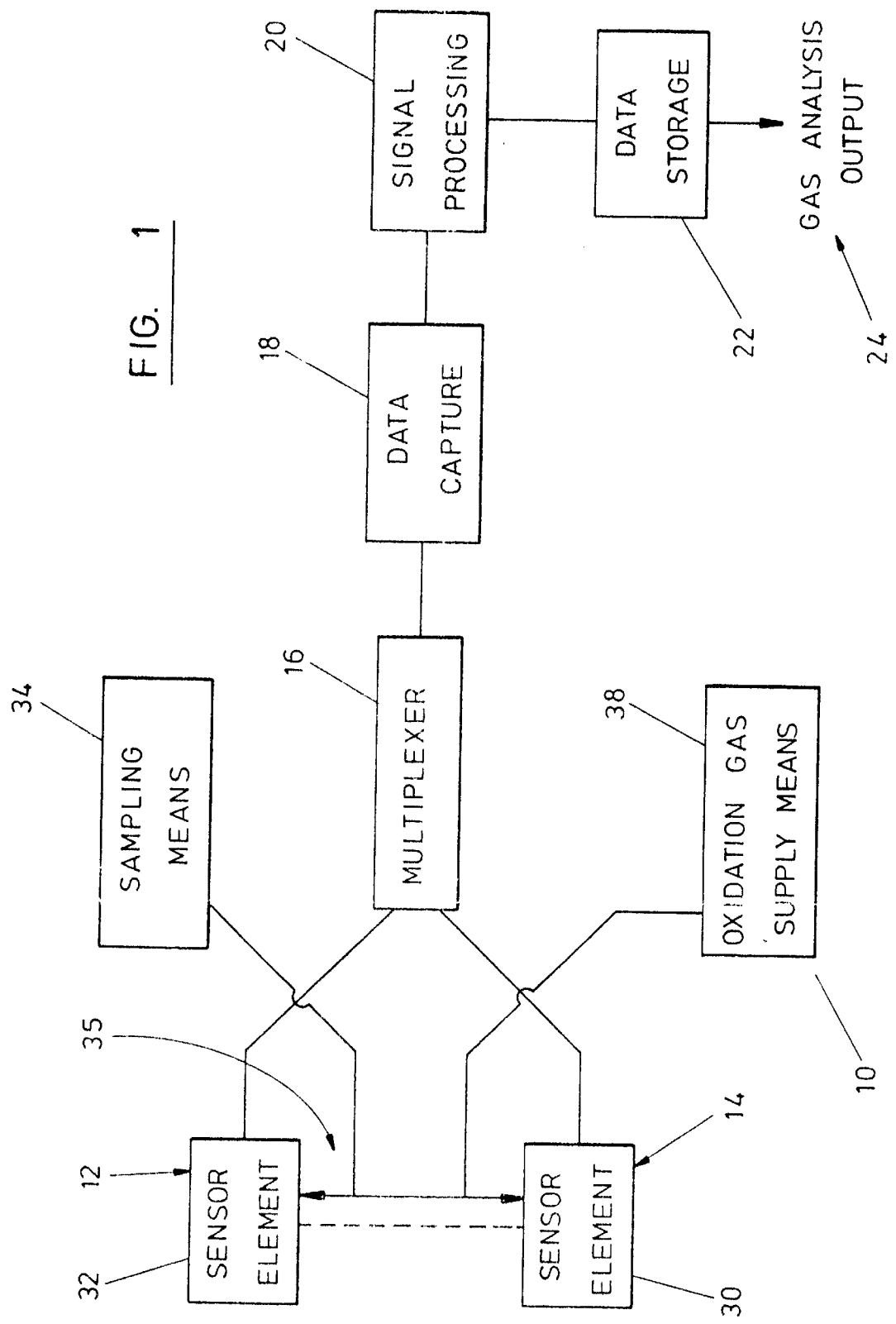
FIG. 1 shows in functional block diagram form an embodiment of apparatus according to the invention.

As shown in the drawings, apparatus 10 for analysis for particulate content of gases comprises sensor elements 12, 14, a multiplexer 16, a data capture system 18, signal processing apparatus 20 together with data storage means 22 and gas analysis output means 24.

These general elements of the apparatus will now be described in more detail.

Figure 2:
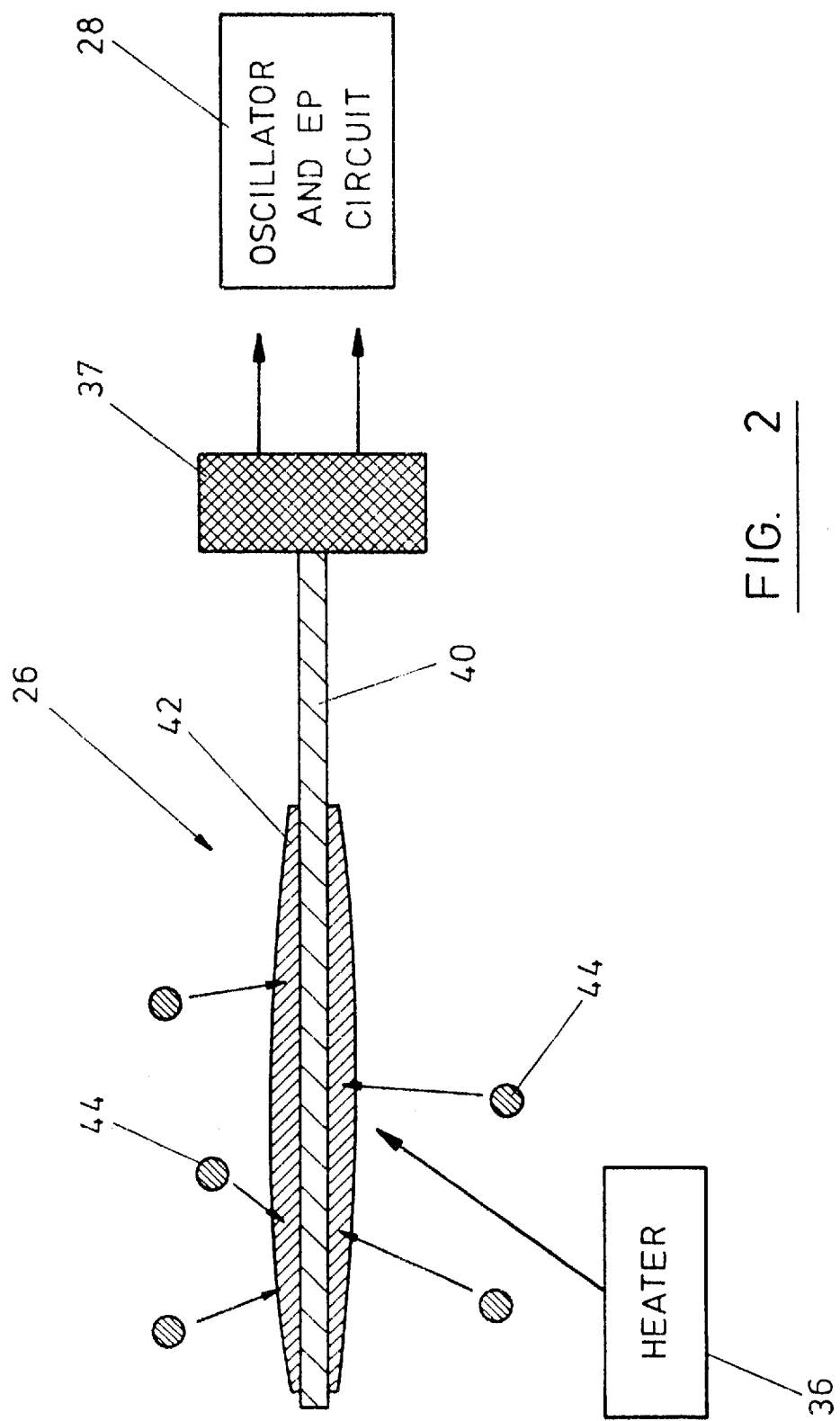
FIG. 2 shows an elevation view of an electrode forming part of the apparatus of FIG. 1.

Sensor elements 12 and 14 represent two of an optional range of elements for analysis of a variety of gases. Each sensor element comprises an electrode 26 as shown in FIG. 2 coupled to an oscillator and electrostatic precipitator circuit 28.

Each sensor element 12, 14 has electrode 26 mounted within a glass envelope indicated at 30, 32 in FIG. 1 to which a gas to be analyzed is supplied by sampling means 34.

Sampling means 34 comprises known apparatus for extracting a volumetrically controlled sample from a gas supply and adapted to deliver same to envelopes 30, 32 containing electrodes 26.

The electrode 26 and the associated electrostatic precipitation circuit 28 constitute removal means adapted to remove particles from the gas sample delivered to envelope 30 or 32 by sampling means 34. The electrode performs the removal step by electrostatic precipitation. It will also be understood that the removal means 26 and 28 also constitute deposition means adapted to deposit the particles on a substrate constituted by the electrode 26.

Further in relation to terminology employed in the definition of the present invention, there is provided further removal means adapted to remove deposited particles from the substrate or electrode 26, and such further removal means is constituted by a heater 36 which effects such removal in combination with oxidation gas supply means 38 which is adapted to supply an oxidizing gas mixture to the envelopes 30, 32 for a purpose to be more fully described below, in a manner analogous to sampling means 36.

Finally, it will be understood that circuits 16, 18, 20 and 22 provide a measurement function in relation to sensor elements 12 and 14 enabling measurement of the step of removal of particles from electrode 26 by the above-mentioned oxidation step for the determination of the particulate content of a gas being analyzed.

Turning now to a more detailed description of the above-mentioned main features of the apparatus 10, sensor elements 12 and 14 will now be more fully described with reference to FIGS. 1 and 2.

Sensor elements 12 and 14 comprise electrodes 26 as shown in FIG. 2 mounted at 37, respectively, in envelopes 30, 32 which are connected to sampling means 34 and the oxidation gas supply means 38. Electrode 26 is in the form of a piezoelectric crystal comprising an AT-cut 10-megahertz crystal 40 having gold-plated electrodes and connected to oscillator circuit 28. Crystal 40 has a coating 42 of a catalytic metal, e.g., platinum or antimony, and forms the anode in the electrostatic precipitator circuit 28. In use, electrode 26 causes particulate matter (shown diagrammatically at 44) to become charged and to move toward and adhere to crystal 40. Crystal 40 becomes loaded with the particulate matter to an extent that reflects the particulate density in the gas mixture to be analyzed. This mass loading of the crystal 40 produces a measurable negative shift (reduction) in the oscillation frequency of crystal 40 in association with oscillator circuit 28. A frequency shift of the order of some hundreds of hertz can be expected.

Turning to FIG. 1 of the drawings, it will be seen that sensor elements 12 and 14 are shown connected to multiplexer 16. The multiplexer and following data processing stages 18, 20 and 22 are adapted to receive frequency information from electrode 26. For simplicity of illustration in FIG. 1, the oscillator and electrostatic precipitator circuits 28 seen in FIG. 2 are not shown. It is to be understood that, of course, these circuits remain in operational connection to electrode 26 in accordance with the requirements of the analysis process described herein.

Turning now to the general mode of operation of apparatus 10, this is as follows. Sampling means 34 delivers the gas to be analyzed to envelopes 30, 32 and thus to the electrodes 26 therein. These effect an electrostatic deposition of particulate content of the gas samples onto the material of the electrode where it is captured by the catalytic coating 42. Sampling means 34 comprises a pump for gas delivery purposes. It is believed that the construction and operation of the oscillator and electrostatic precipitator circuit 28 will be well known to those skilled in the technical field and, therefore, these are not further described here.

Oscillator circuit 28 is activated to establish a preliminary oscillation frequency prior to the electrostatic deposition stage. Then the electrostatic precipitator circuit is energized to effect such precipitation, whereupon there is a frequency shift as described above, in accordance with the mass of particulate deposited.

After this deposition step in relation to particulate matter from the gas sample, there follows the step of removal of the particulate from the electrodes 26. This is effected by activating the supply 38 of oxidation gas so that the gas to be sampled is flushed out and electrode 26 is surrounded by an oxidizing atmosphere. Thereupon heater 36 is energized. The heater may, for example, be a laser beam, focused upon the electrode, whereby the deposited particles are caused to be removed from the electrode by oxidation in the elevated temperature and oxidizing atmosphere conditions thus-provided.

During this process of particulate removal from the electrode 26, the oscillation frequency of electrodes 26 and oscillator circuit 28 continue to be monitored by the data-processing system 16, 18, 20 and 22. The resultant shift in oscillation frequency occurring in such a situation is shown, for one typical example, in FIG. 3 where the mass of material deposited is plotted against time. This plot is obtained during the oxidation step, since mass can be seen here to reduce substantially with time.

Figure 3:
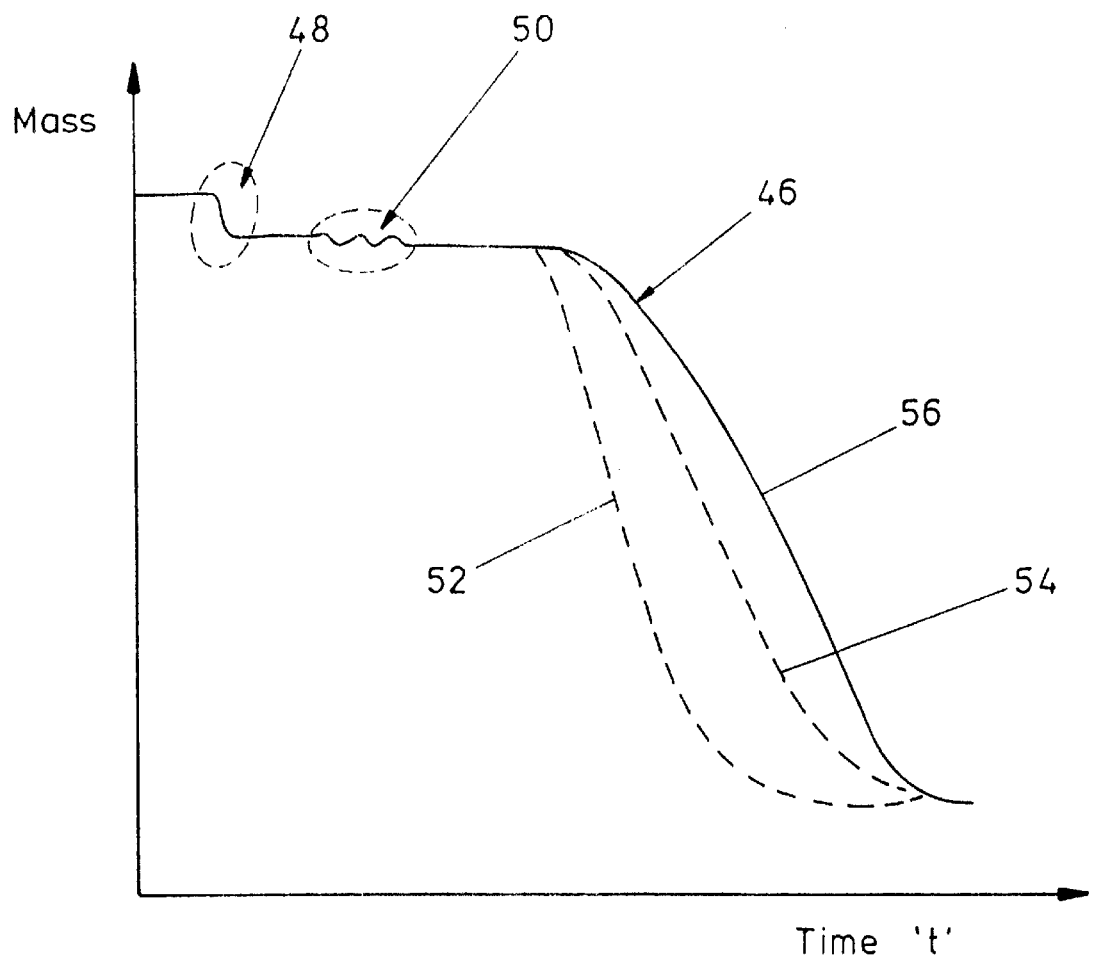
FIG. 3 shows a plot of mass against time for a part of the process carried out by the apparatus of FIGS. 1 and 2, relating to removal of particles from the electrode of FIG. 2.

As the particulate material mass loading on crystals 40 reduces, the oscillation frequency correspondingly increases. The graphic presentation in FIG. 3 is derived from the frequency shift information provided to the data handling system, 16, 18, 20 and 22. The profile of the plot 46 enables interpretation of the presence of particulates on a qualitative basis. For example, the dip shown at 48 in FIG. 3 corresponds to the removal of the soluble organic fraction (SOF) from the electrode. The features of the plot identified at 50 are characteristic of the break-up of particulate content. The method permits analysis of the agglomeration (total mass of material deposited and its removal), and the sulphate content and the soluble organic fraction. The shape of the curve at location 50 is characteristic of the break-up of agglomerated particulate matter.

After use, flushing or de-gassing of the sensor elements 12 and 14 can be accomplished by reversing the polarity of the precipitator and flushing the envelopes 30, 32 with nitrogen.

In the above embodiment, the sensor elements 30 and 32 may be provided with specific abilities to absorb and permit analysis of specific hydrocarbons, or a family of hydrocarbons, by varying the material of the coating on the electrode. Accordingly, if so required, an array of similar piezoelectric electrodes 26 may be provided in order to deal with the analysis of particular gas constituents. Such provision is indicated at 35 in FIG. 1.

In FIG. 3 the alternative curve dip profiles shown at 52, 54 and 56 enable interpretation of specific constituent materials in the same manner as the profiles shown at 48 and 50, and notably in relation to the particle size of an identified constituent, the dip profiles 52, 54, 56 each being characteristic of a range of particle sizes. Such interpretation is effected by the data processing apparatus shown in FIG. 1, namely multiplexer 16, data capture system 18, signal processing system and data storage system 22, on the basis of prior test work using known gas samples of known particle size.

In a further embodiment, there may be employed a chromatograph (not shown) in association with the thermogravimetric analysis apparatus described above, in order to provide additional data in relation to the analysis of the gas in question.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A method of analysis of particulate content of gases comprising:
   a) sampling a gas to be analyzed to provide a gas sample;
   b) removing particles from said sample by causing the particles to be deposited by electrostatic precipitation on a frequency-responsive substrate;
   c) causing at least some of the deposited particles to be at least partially removed from the substrate; and
   d) applying a frequency monitoring technique to the step of at least partial removal of the particles from the substrate in order to determine information concerning the particulate content of the gas to be analyzed.

2. A method according to claim 1, wherein the electrostatic precipitation includes precipitating the particles on a substrate which includes a metal-coated piezoelectric crystal forming an anode in the precipitation step.

3. A method according to claim 2, wherein the metal coating on the anode is a catalytic metal.

4. A method according to claim 1, wherein the step of removal of the particles from the substrate includes oxidizing the particles by heating the substrate in an oxidizing atmosphere.

5. A method according to claim 1, wherein the step of applying a frequency monitoring technique to the step of removal of the particles from the substrate includes employing the substrate as an electrode in an electrostatic precipitator circuit and connecting the electrode to an oscillator circuit and determining the frequency of oscillation as a measure of the mass of particles remaining on the substrate as oxidation proceeds.

6. A method according to claim 5, wherein the step of determining the frequency of oscillation includes monitoring changes in the oscillation frequency of the circuit as the measure of the mass of the particles remaining on the substrate.

7. A method according to claim 6, wherein by the step of applying a frequency monitoring technique includes determining changes in gradient or profile of a graph of the rate of change of mass of the substrate as a basis for determining the identity and/or particle size of particulate materials deposited on and removed from the substrate.

8. A method of analysis of the particulate content of a gas to be analyzed comprising the steps of: at least partially removing from a substrate particles deposited thereon from a gas sample by electrostatic precipitation, and applying a frequency monitoring technique to the step of removal of particles from the substrate so as to determine information concerning the particulate content of the gas to be analyzed.

9. Apparatus for the analysis of particulate content of gases comprising:
   a) sampling means adapted to sample a gas to be analyzed to produce a gas sample;
   b) a sensor including electrostatic precipitation apparatus and a frequency-responsive substrate disposed to remove particles from the sample by deposition on the substrate by electrostatic precipitation;
   c) removal means adapted to remove from the substrate at least partially at least some of the particles deposited thereon; and
   d) frequency-monitoring measurement means adapted to measure one or more aspects of the at least partial removal of particles from the substrate in order to determine information concerning the particulate content of the gas to be analyzed.

10. Apparatus according to claim 9, wherein the electrostatic precipitation apparatus includes a metal-coated piezoelectric crystal forming an anode in the electrostatic precipitation apparatus.

11. Apparatus according to claim 10, wherein the metallic coating of the anode includes a catalytic metal.

12. Apparatus according to claim 9, wherein said removal means includes heating means for the substrate and gas supply means adapted to supply an oxidizing atmosphere to said sensor, whereby the particles thereon can be heated in an oxidizing atmosphere to effect oxidation thereof.

13. Apparatus according to claim 9, wherein said measurement means includes an oscillator circuit, and wherein said substrate forms an electrode connected as an anode to said oscillator circuit, and further including frequency determining means being provided to determine the frequency of oscillation of said oscillator circuit as a measure of the mass of particles remaining on said substrate as oxidation proceeds.

14. Apparatus according to claim 13, wherein the frequency-monitoring measurement means includes means to monitor changes in the oscillation frequency as the measure of the mass of particles deposited.

15. Apparatus according to claim 14, wherein said measurement means includes interpretation means adapted to interpret data obtained by said means to monitor for determining changes in gradient or profile of a graph of rate of change of mass of said substrate as a basis for determining the identity and/or quantitative presence of materials deposited on and removed from said substrate.

16. Apparatus for the analysis of particulate content of gases comprising: electrostatic precipitation apparatus and a substrate adapted to receive particles to be deposited thereon from a sample of the gas to be analyzed by electrostatic precipitation, removal means adapted to remove at least partially at least some of the deposited particles, and frequency monitoring measurement means responsive to said removal means to determine information concerning the particulate content of the gas to be analyzed on the basis of the removal of particles.

* * * * *